US007340083B2

United States Patent
Yuan et al.

(10) Patent No.: US 7,340,083 B2
(45) Date of Patent: Mar. 4, 2008

(54) METHOD AND SYSTEM FOR ATHEROSCLEROSIS RISK SCORING

(75) Inventors: Chun Yuan, Belleuve, WA (US); Thomas S. Hatsukami, Mercer Island, WA (US); Renu Virmani, Chevy Chase, MD (US); Jianming Cai, Beijing (CN); William S. Kerwin, Seattle, WA (US); Marina S. Ferguson, Seattle, WA (US)

(73) Assignee: University of Washington, Seattle, WA (US)

( * ) Notice: Subject to any disclaimer, the term of this patent is extended or adjusted under 35 U.S.C. 154(b) by 470 days.

(21) Appl. No.: 11/172,415

(22) Filed: Jun. 29, 2005

(65) Prior Publication Data

US 2007/0003116 A1   Jan. 4, 2007

(51) Int. Cl.
*G06K 9/00* (2006.01)
*G06F 7/60* (2006.01)
*G06F 17/10* (2006.01)

(52) U.S. Cl. .......................................... 382/128; 703/2
(58) Field of Classification Search ................ 382/128; 703/2
See application file for complete search history.

(56) References Cited

U.S. PATENT DOCUMENTS

| 6,763,261 B2 | 7/2004 | Casscells, III et al. |
| 6,816,743 B2* | 11/2004 | Moreno et al. .............. 600/473 |
| 7,149,331 B1* | 12/2006 | Kaufman et al. ............ 382/128 |
| 2003/0215124 A1* | 11/2003 | Li .............................. 382/131 |
| 2004/0022359 A1* | 2/2004 | Acharya et al. .......... 378/98.11 |
| 2004/0133100 A1* | 7/2004 | Naghavi et al. ............ 600/425 |

OTHER PUBLICATIONS

Rumberger, John A., Bruce H. Brundage, Daniel J. Rader, and George Kondos. "Electron Beam Computed Tomographic Coronary Calcium Scanning: A Review and Guidelines for Use in Asymptomatic Persons". Mayo Clinic Proceedings: 1999. vol. 74. pp. 243-252.*

Bassiouny, Hisham S., Yashuhiro Sakaguchi, Susanne A. Mikucki, James F. McKinsey, Giancarlo Piano, Bruce L. Gewertz, and Seymour Glagov. "Juxtaluminal Location of Plaque Necrosis and Neoformation in Symptomatic Cariod Stenosis". Journal of Vascular Surgery. vol. 26, No. 4. pp. 585-594.*

(Continued)

*Primary Examiner*—Brian Werner
*Assistant Examiner*—Damon Conover
(74) *Attorney, Agent, or Firm*—Christensen O'Connor Johnson Kindness PLLC

(57) ABSTRACT

A method for characterizing the risk associated with atherosclerosis is disclosed. The method uses one or more images of cross-sections of the artery or other vessel of interest to identify and locate components of the atherosclerotic deposit, including any hemorrhage, necrotic core, and calcification, and to determine the status and composition of the fibrous cap. In one embodiment, high resolution MRI images are utilized, although other imaging modalities may alternatively be used. A simple scoring system is applied that accounts for the presence of these components and more heavily weights the presence of these components in the juxtaluminal portion of the deposit. The status of the fibrous cap (intact or ruptured) and the composition of the fibrous cap (collagen or mixed tissue) are also incorporated into a final atherosclerosis risk score.

18 Claims, 3 Drawing Sheets

OTHER PUBLICATIONS

Kerwin, William, Chao Han, Baocheng Chu, Dongxiang Xu, Ying Luo, Jenq-Neng Hwang, Thomas Hatsukami, and Chun Yuan. "A Quantitative Vascular Analysis System for Evaluation of Atherosclerotic Lesions by MRI". Proceedings of Medical Image Computing and Computer-Assisted Intervention: 2001. Utrecht, The Netherlands. pp. 786-794.*

Yuan, Chun, Lee M. Mitsumori, Kirk W. Beach, and Kenneth R. Maravilla. "Carotid Atherosclerotic Plaque: Noninvasive MR Characterization and Identification of Vulnerable Lesions". Radiology: 2001. vol. 211. pp. 285-299.*

Yuan et al. "In Vivo Accuracy of Multispectral Magnetic Resonance Imgaing for Identifying Lipid-Rich Necrotic Cores and Intraplaque Hemorrhage in Advanced Human Carotid Plaques". Circulation: 2001. vol. 104. pp. 2051-2056.*

Toussaint, Jean-Francois, Glenn M. LaMuraglia, James F. Southern, Valentin Fuster, and Howard L. Kantor. "Magnetic Resonance Images Lipid, Fibrous, Calcified, Hemorrhagic, and Thrombotic Components of Human Atherosclerosis In Vivo". Circulation: 1996. vol. 94. pp. 932-938.*

Saam, T., M.S. Ferguson, V.L. Yarnykh, N. Takaya, D. Xu, N.L. Polissar, T.S. Hatsukami, and C. Yuan. "Quantitative Evaluation of Carotid Plaque Composition by In Vivo MRI". Artheriosclerosis, Thrombosis, and Vasular Biology: 2005. vol. 25. pp. 234-239.*

Hatsukami, Thomas S., William Kerwin, Jian-Ming Cai, X.J. Kang, Nayak Polissar, Marina Ferguson, Randy Small, Xue-Qiao Zhao, and Chun Yuan. "High-Resolution Magnetic Resonance Imaging of Carotid Atherosclerosis". International Congress Series 1262 (2004). Elsevier. pp. 95-98.*

Hiro, Takafumi, Takashi Fujii, Kyounori Yasumoto, Takashige Murata, Akihiro Murashige, and Masunori Matsuxaki. "Detection of Fibrous Cap in Atherosclerotic Plaque by Intravascular Ultrasound by Use of Color Mapping of Angle-Dependent Echo-Intensity Variation". Circulation: 2001. vol. 103. pp. 1206-1211.*

Zhi-Yong, Li, Simon P.S. Howarth, Tjun Tang, and Jonathan H. Gillard. "How Critical is Fibrous Cap Thickness to Carotid Plaque Stability?: A Flow-Plaque Interaction Model". Stroke: May 2006. pp. 1195-1199.*

Devuyst, G., et al., "Ultrasound Measurement of the Fibrous Cap in Symptomatic and Asymptomatic Atheromatous Carotid Plaques," *Circulation*, pp. 2776-2782, May 31, 2005.

Hatsukami, T.S., et al., "Visualization of Fibrous Cap Thickness and Rupture in Human Atherosclerotic Carotid Plaque In Vivo With High-Resolution Magnetic Resonance Imaging," *Circulation*, pp. 959-964, Aug. 29, 2000.

Kampschulete, A., et al., "Differentiation of Intraplaque Versus Juxtaluminal Hemorrhage/Thrombus in Advance Human Carotid Atherosclerotic Lesions by In Vivo Magnetic Resonance Imaging," *Circulation*, pp. 3239-3244, Nov. 16, 2004.

Lovett, J.K., and P.M. Rothwell, "Site of Carotid Plaque Ulceration in Relation to Direction of Blood Flow: An Angiographic and Pathological Study," *Cerebrovasc. Dis. 16*:369-375, 2003.

Virmani, R., et al., "Lessons From Sudden Coronary Death: A Comprehensive Morphological Classification Scheme for Atherosclerotic Lesions," *Arterioscler. Thromb. Vasc. Biol.*, pp. 1262-1275, May 2000.

Yuan, C., et al., "Identification of Fibrous Cap Rupture With Magnetic Resonance Imaging is Highly Associated With Recent Transient Ischemic Attack or Stroke," *Circulation*, pp. 181-185, Jan. 15, 2002.

Yuan, C., and W.S. Kerwin, "MRI of Atherosclerosis," *J. Cardiovasc. Magn. Reson. 19*: 710-719, 2004.

* cited by examiner

METHOD AND SYSTEM FOR ATHEROSCLEROSIS RISK SCORING

STATEMENT OF GOVERNMENT LICENSE RIGHTS

The U.S. Government has a paid-up license in this invention and the right in limited circumstances to require the patent owner to license others on reasonable terms as provided for by the terms of Grant No. RO1HL56874 awarded by the National Institutes of Health.

FIELD OF THE INVENTION

The present invention relates generally to methods for assessing a patient's risk associated with atherosclerosis and, more particularly, to clinically efficient methods for characterizing such risks.

BACKGROUND OF THE INVENTION

Cardiovascular disease secondary to atherosclerosis is the leading cause of mortality and morbidity worldwide. Growing evidence suggests that the decisive factor determining increased risk for atherosclerotic plaque to cause clinical events is plaque composition rather than the degree of luminal narrowing as measured by angiography.

Atherosclerosis is a form of arteriosclerosis that is characterized by the deposition of plaques containing cholesterol and lipids on the innermost layer of the walls of arteries. Atherosclerosis is currently understood to be a chronic inflammatory disease rather than an inevitable degenerative aging process. The condition usually affects large- and medium-sized arteries. Although such plaque deposits can significantly reduce the blood's flow through an artery, the more serious risk is generally associated with the instigation of an acute clinical event through plaque rupture and thrombosis. In particular, serious damage can occur if an arterial plaque deposit becomes fragile and ruptures, fissures, or ulcerates. Plaque rupture, fissure, or ulcer can cause blood clots to form that block or occlude blood flow and/or break off and travel to other parts of the body. If such blood clots block a blood vessel that feeds the heart, it causes a heart attack. If the blood clot blocks a blood vessel that feeds the brain, it causes a stroke. Similarly, if blood supply to the arms or legs is reduced, it can cause difficulty in walking or light exercise and other collateral damage. Recent studies indicate that thrombotic complications of atherosclerosis remain the leading cause of morbidity and mortality in Western society.

Atherosclerosis may start in childhood and may progress at varying rates as a person ages. In some people, atherosclerosis progresses rapidly, even at a relatively young age. Tobacco smoke greatly worsens atherosclerosis and speeds its growth in the coronary arteries, the aorta, and arteries in the legs. Although some factors that correlate with a higher risk of atherosclerosis are not controllable, such as gender and family history, other correlated risk factors are controllable—including, for example, high blood cholesterol levels, exposure to tobacco smoke, high blood pressure, obesity, and physical inactivity.

The presence and extent of plaque build up in an individual's arteries can be detected using a variety of techniques that are well known in the field including, for example, magnetic resonance imaging ("MRI"), computed tomography ("CT"), X-ray angiography, and ultrasound. Prior art methods for assessing an individual's risk of a clinically significant event such as a stroke or heart attack related to atherosclerotic deposits in an individual's arteries have primarily been directed to evaluating the effect that the plaque deposit has on the blood flow through the artery.

The risk associated with rupture, fissure, or ulceration of plaque, however, may be present even when the plaque deposit does not significantly reduce the flow of blood in an artery. For example, arteries and other blood vessels will sometimes expand or "remodel" in the region of a significant atherosclerotic plaque deposit such that the lumen area does not decrease sufficiently to significantly reduce blood flow. If the plaque ruptures, it may nevertheless create a blood clot that may travel to a critical area to cause a clinical event. The susceptibility of a plaque deposit to structural failure is difficult to determine.

In a clinical context it is often useful to evaluate a particular patient or condition using a simplified scoring system that takes into account a large amount of data and a number of different factors in a simplified manner to rapidly characterize the patient's risk. Such methods can provide a rapid means for evaluating a patient's condition and the urgency of providing appropriate treatments. A well known example of such a scoring system is the Apgar scale ubiquitously used to rapidly judge the health of a new born baby wherein, at one minute and again at five minutes after birth, the infant is evaluated for heart rate, respiration, muscle tone, reflex response, and skin color. Each factor is given a score between zero and two and the scores are added up to provide an immediate assessment of the infant's overall health that is useful in the clinical setting.

With regard to assessing the risk associated with atherosclerosis after imaging a section of a patient's artery having a significant plaque deposit, in the past a medical professional might take hours reviewing the images identifying structures over the region of interest. Such evaluations are clearly not suitable in a clinical setting wherein a rapid evaluation is required.

Therefore, there remains a need for a relatively simple method and system for assessing the risk associated with an atherosclerotic plaque deposit in a patient's artery.

SUMMARY OF THE INVENTION

This invention relates to a scoring system that summarizes key factors of atherosclerotic plaque vulnerability into a quantitative number that describes the current status of the lesion and is directly linked to risk of causing clinical events and/or rapid progression of the disease. This unique scoring approach accounts for juxtaluminal characteristics of atherosclerotic plaque including the status of the fibrous cap and the presence of any or all main plaque tissue components such as hemorrhage, lipid rich necrotic core, and calcification, as well as inflammatory activity, and their relative distance to the vessel lumen. This plaque information is non-invasively acquired in vivo, for example, using magnetic resonance imaging. A primary application of the atherosclerotic risk scoring can be found in the clinical diagnosis of human carotid atherosclerosis.

In an embodiment of the invention, one or more cross-sectional images of an artery are taken, for example, by magnetic resonance imaging, computed tomography, ultrasonics, positron emission tomography, or the like, including possibly using combinations of one or more of these imaging modalities. Components of the plaque—such as necrotic core, hemorrhage, and calcification—are identified and located relative to the juxtaluminal region of the artery. The image is also analyzed to determine the status and composition of the fibrous cap. For example, the fibrous cap may be collagen or mixed tissue (sometimes referred to as "loose matrix") and may be intact or ruptured. An atherosclerotic risk score is then calculated that characterizes the risk associated with the imaged portion of the artery that is dependent on the fibrous cap status and composition and the present of the identified components in the juxtaluminal region of the artery.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
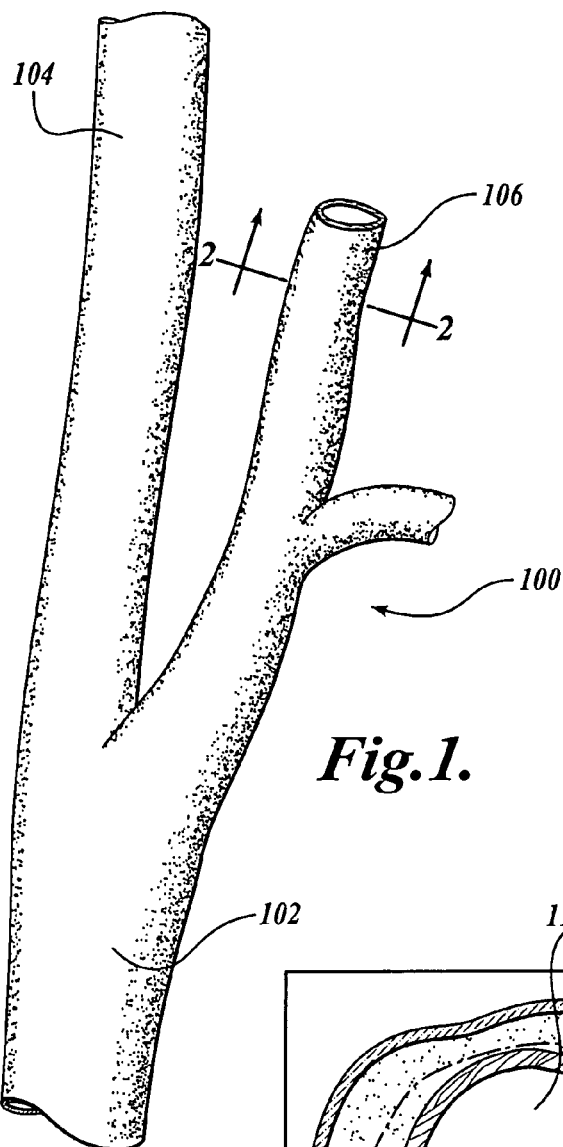
FIG. 1 is a sketch of an exemplary portion of a typical carotid artery.

Histological studies in various vascular beds have established that plaque tissue composition and distribution may strongly influence its clinical course and the likelihood that an atherosclerotic deposit will precipitate a clinical event. For example, a thin fibrous cap covering a large, lipid-rich necrotic core appears to be a clear marker of vulnerable plaque. The "fibrous cap" is a distinct layer of connective tissue that typically covers the lipid core of a plaque deposit. The fibrous cap generally comprises smooth muscle cells in a collagenous-proteoglycan matrix, with varying degrees of infiltration by macrophages and lymphocytes.

A thinning fibrous cap indicates weakened structural integrity and possible future rupture that may lead to an embolic event. In a study of patients using carotid magnetic resonance imaging ("MRI") to image a portion of the carotid artery prior to undergoing a carotid endarterectomy, the prevalence of fibrous cap rupture, juxtaluminal hemorrhage (thrombus) and juxtaluminal calcification was significantly higher in symptomatic plaque deposits as compared to asymptomatic deposits. Furthermore, in a landmark study based on coronary autopsy specimens, ruptured fibrous cap, calcium nodules, and endothelial erosions were highly correlated with sudden cardiac death. (Virmani et al., Lessons From Sudden Coronary Death: A Comprehensive Morphological Classification Scheme for Atherosclerotic Lesions, *Arterioscler. Thromb. Vasc. Biol.* 20:1262-1275, 2000.) These features all involve the interface between the plaque and the lumen or the plaque region immediately adjacent to the lumen (the "juxtaluminal region"). Thus, this juxtaluminal region is crucial to improved identification and understanding of vulnerable plaques.

The present invention is directed in part to a method for combining assessments of plaque composition with quantitative or qualitative evaluation of the juxtaluminal characteristics to produce a new, clinically useful, lesion scoring system. It is contemplated that the new scoring system may be adjusted to be specific to the particular artery of interest—for example, the carotid arteries, coronary arteries, and aorta. However, the important aspect is that the scoring system of the present invention utilizes the variables that are important to identifying "vulnerable plaques," assigns relative weights based on proximity to the vessel lumen, and combines the variables to produce a simple score that reflects or characterizes the risk that the identified plaque will cause thrombo-embolic events, as well as indicating the likely clinical course of the deposit.

In particular, the method for scoring a patient's atherosclerosis is based on an analysis of an image or set of images of a cross-section of the artery showing an atherosclerotic deposit. The image or set of images must have sufficient resolution and discrimination to identify the components of the plaque deposit and their location relative to the vessel lumen. In the currently preferred embodiment the cross-sectional image(s) is substantially transverse to the axial direction of the vessel or artery, although it is contemplated that the method may be utilized with cross-sectional images that are parallel to the vessel or at a skewed angle with respect to the vessel axis. In the currently preferred exemplary method described herein, the cross-sectional image is taken at one or more selected axial positions, substantially perpendicular to the axis of the vessel.

High-resolution MRI, as a noninvasive imaging tool, has proven to be an imaging modality with excellent capability for discriminating tissues of the carotid plaque, including the status and composition of the fibrous cap, and the location of lipid-rich necrotic core, calcification, and hemorrhage within the deposit. MRI is currently superior to other imaging modalities in distinguishing soft tissue contrast and has been demonstrated as a useful tool in identifying morphological and compositional features of atherosclerotic plaque both in vitro and in vivo. For example, by using multiple contrast weightings available in MRI, complex plaque tissue components have been accurately characterized and identified. MRI has also been shown to be capable of identifying the fibrous cap in atherosclerotic carotid arteries in vivo. For example, high resolution in vivo carotid plaque imaging with a spatial resolution of 0.5×0.5×2 $mm^3$ has been obtained using a phased-array carotid coil in a 1.5T whole body scanner. Soft plaques containing necrotic cores and/or interplaque hemorrhage have been identified with high sensitivity and specificity, the lumen and outer wall boundaries identified, and the fibrous cap and its thickness visualized with gradient echo based time-of-flight imaging.

Although the currently preferred method for imaging an artery uses high-resolution MRI, it is contemplated that the present invention may be practiced using other imaging techniques, including for example, computed tomography ("CT"), ultrasonics, positron emission tomography ("PET"), and the like, including combinations of these imaging techniques. Any imaging technology or combinations of technologies, that provide sufficient resolution and discrimination to identify and locate the compositions of the plaque deposit in vivo and to evaluate the fibrous cap is suitable for practicing the present invention.

Figure 2:
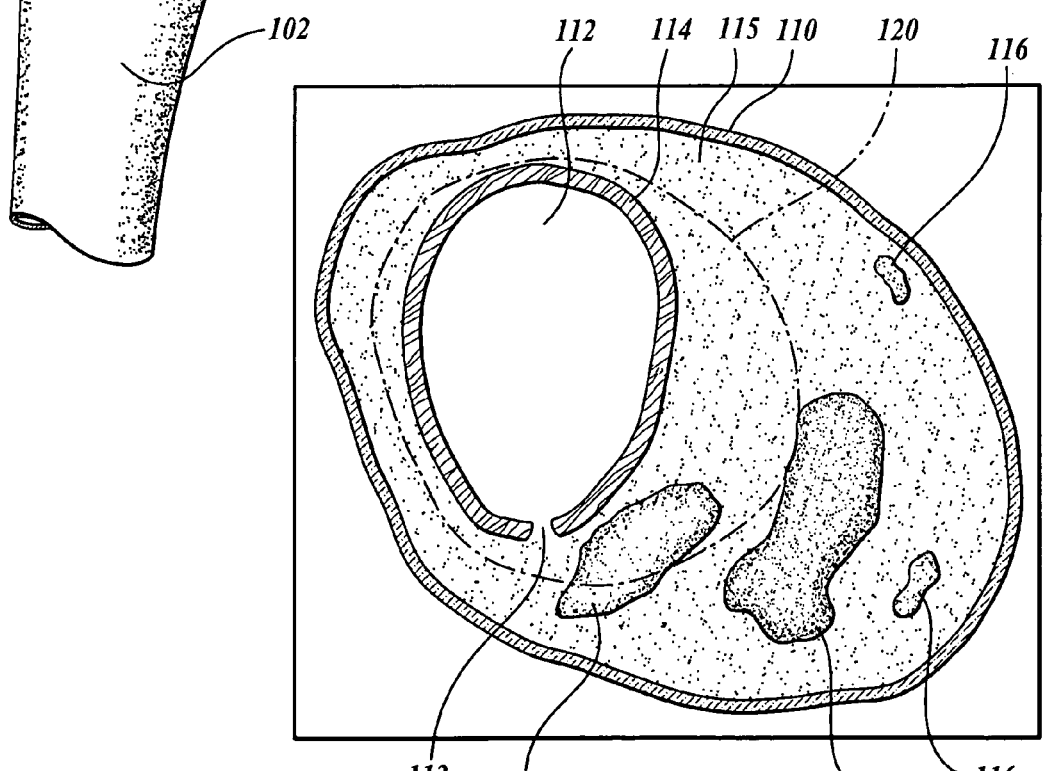
FIG. 2 is a representative sketch of a magnetic resonance image of a transverse cross-section through section 2-2 of the external carotid artery shown in FIG. 1.

Refer now to FIG. 1, which shows a sketch of a portion of a carotid artery 100 showing the bifurcation of the common carotid artery 102 into the internal carotid artery 104 and the external carotid artery 106. FIG. 2 shows a sketch of an exemplary MRI image taken through a cross-section of the external carotid artery 106 at section 2-2 of FIG. 1. It should be appreciated that the sketch of FIG. 2 is a simplified depiction of a high-resolution MRI image, presented here to facilitate understanding of the present invention. In practice, a clinician or other healthcare professional may examine more than one image to identify specific features of the atherosclerotic deposit. For example, a skilled clinician can identify in the MRI image(s) the artery 106, outer wall 110, the atherosclerotic plaque 115 therein, and other components of the plaque 115, as discussed below. Alternatively, image analysis software may be used to identify or facilitate identification of these components.

In the exemplary sketch of FIG. 2, the atherosclerotic plaque 115 is substantial. A lumen 112 provides a flow path for the blood and a relatively narrow fibrous cap 114 forms the interface between the lumen 112 blood flow and the rest of the plaque deposit 115. The fibrous cap 114 may be ruptured, as indicated at 113, which may appear in the MRI image as a light or a dark area on the fibrous cap 114. The plaque 115 may include one or more regions of calcification 116 (two shown), one or more necrotic core region(s) 118 and/or hemorrhage(s) 119.

The status of the fibrous cap 114 can also be determined from the high-resolution MRI image(s) as either ruptured or intact and the fibrous cap component can be determined as collagen or mixed tissue. The location of early or recent hemorrhage 119, necrotic core 118, and calcification 116 can also be identified from the MRI image(s)—in particular, the radial position with respect to the lumen 112, to determine if these components are partially or wholly within the juxtaluminal portion of the plaque deposit 115.

In the current embodiment of the invention, the juxtaluminal portion of the plaque deposit 115 comprises the inner one third of the thickness of the plaque 115, as approximately indicated by the dotted line 120. It is contemplated, however, that other definitions of the juxtaluminal region may be used without departing from the present invention and that the portion of the plaque 115 that is included in the juxtaluminal portion may depend, for example, on the particular artery of interest (e.g., carotid, aortic, etc.). For example, in some instances it may be preferable to define a larger or smaller portion of the plaque 115 as juxtaluminal or a prescribed thickness of the plaque 115 may be characterized as juxtaluminal. It is also contemplated that different definitions of juxtaluminal may be appropriate for the different components.

When the presence and location of the various components (e.g., calcification 116, necrotic core 118, hemorrhage 119) of the plaque deposit 115 and the status and composition of the fibrous cap 114 are determined, simple values are assigned and combined to characterize the risk associated with an imaged plaque deposit 115.

Figure 3:
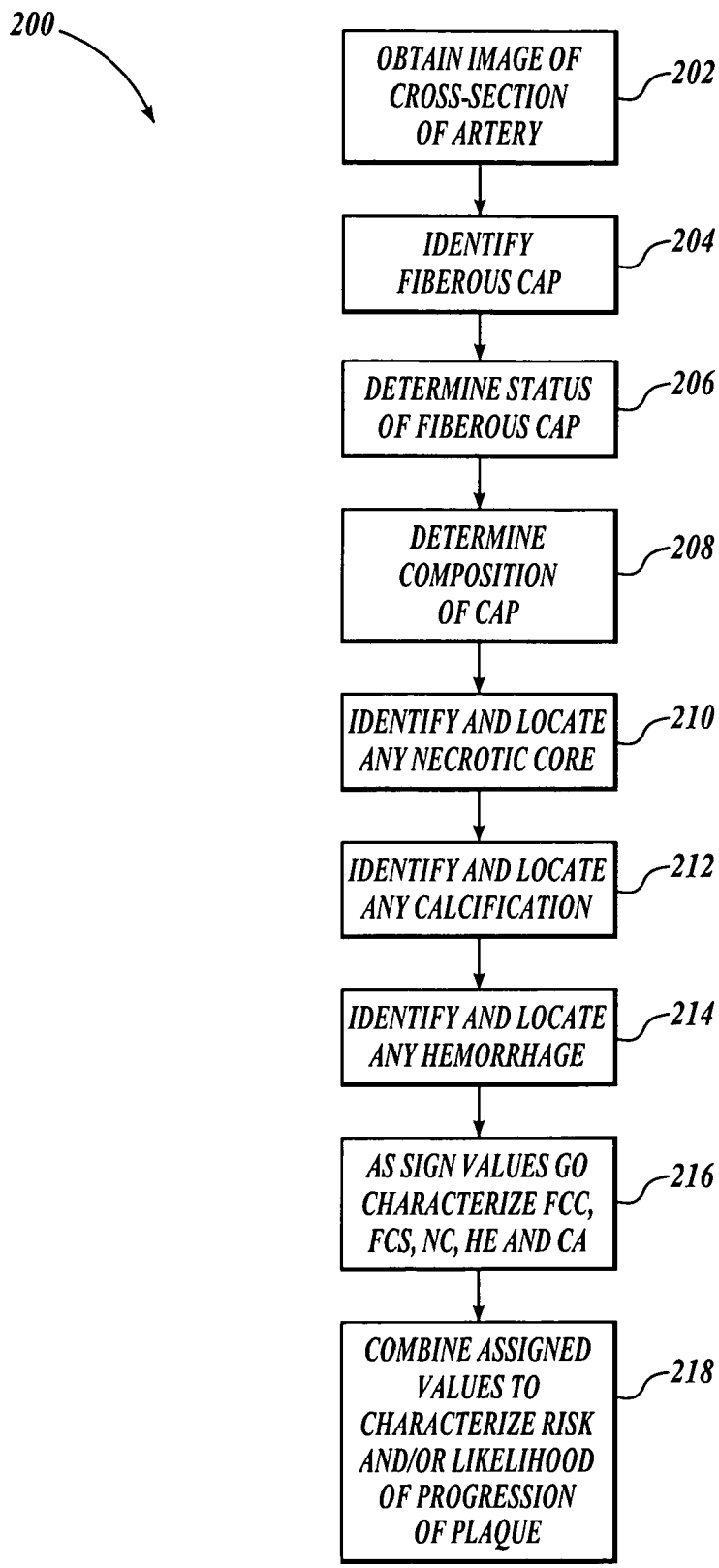
FIG. 3 is a flow chart showing the currently preferred method for scoring the risk associated with an atherosclerotic deposit.

Refer now to FIG. 3, which shows a flow chart of the currently preferred method for scoring the atherosclerotic risk associated with a plaque deposit. Typically, the clinician(s) first obtains one or more images of cross-sections of an artery of interest 202—for example, using MRI, ultrasonics, CT, PET, and/or other imaging modality. The image(s) is then analyzed and, if a plaque deposit is present, the fibrous cap is identified 204, its status (intact or ruptured) is determined 206, and its thickness and/or composition (collagen or mixed tissue) is determined 208. The image(s) is further analyzed to identify and locate any necrotic core 210, calcification 212, and hemorrhage 214. Values are assigned to the features 216 described above—for example, according to the table shown in FIG. 4—and an atherosclerosis risk scoring is calculated 218, for example, as indicated in FIG. 5.

Figure 4:
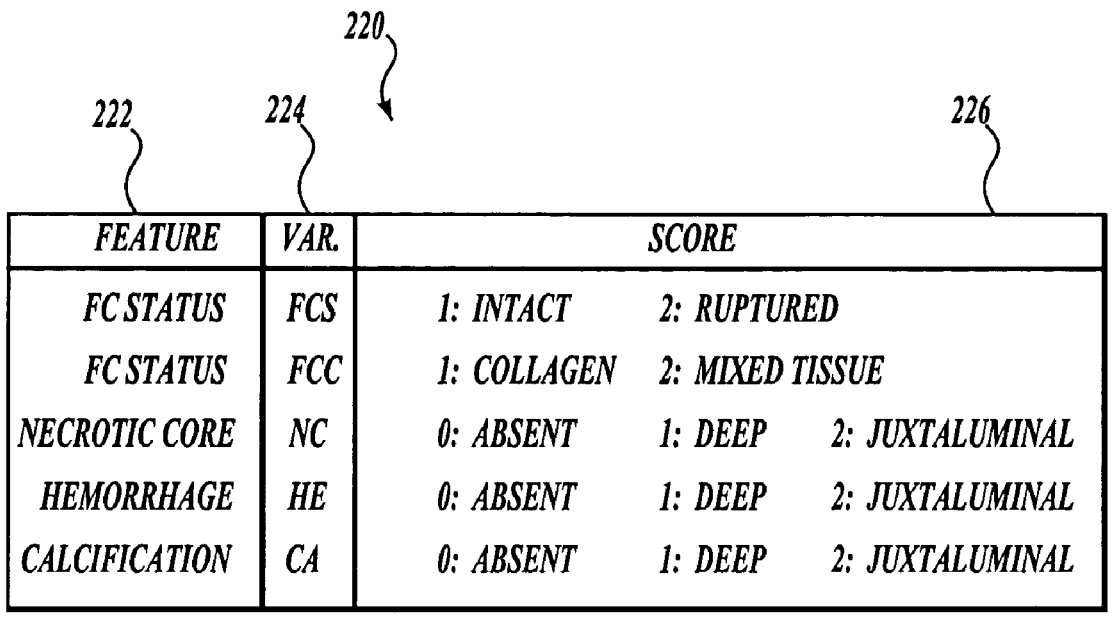
FIG. 4 is a table indicating the currently preferred component scoring for the method shown in FIG. 3.

FIG. 4 presents a table 220 showing the current component scoring system for the features described above 222, a corresponding variable 224, and the condition for assigning a value or scoring each variable 226. If the fibrous cap is intact, FCS is assigned a value of 1; if it is ruptured, then FCS is assigned a value of 2. If the fibrous cap is collagen, FCC is assigned a value of 1; if it is mixed tissue, then FCC is assigned a value of 2. Similarly, if no necrotic core, hemorrhage, and/or calcification is apparent in the image—NC, HE, and CA, respectively—are assigned values of zero. If any of these components are found in the image but in a deep portion of the plaque (i.e., not in the juxtaluminal region), then the respective variable is assigned a value of 1. If any of these components is found in the juxtaluminal region of the plaque deposit, the respective variable is assigned a value of 2. It will be appreciated that this simple scoring system can be accomplished very quickly and easily from examining the MRI image(s) or by automated image analysis software, as is known in the art.

Figure 5:
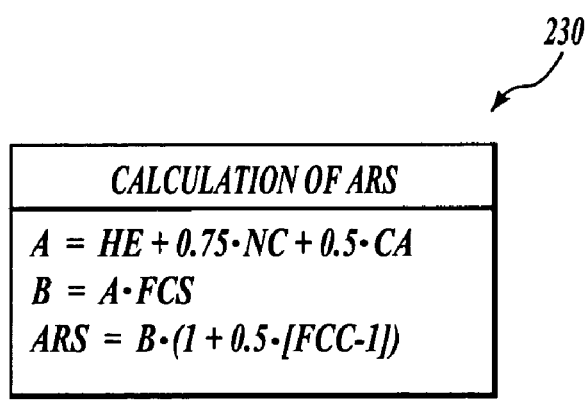
FIG. 5 shows the currently preferred method for combining the component scoring for the method shown in FIG. 3.

Referring now to FIG. 5, the table 230 shows the preferred method for combining the assigned values to generate an atherosclerosis risk score ("ARS"). The ARS characterizes the level of risk associated with a patient's atherosclerosis as indicated by a particular cross section of an artery. In the currently preferred embodiment, an intermediate value of A is calculated by weighting and adding the scores for the plaque components HE, NC, and CA (hemorrhage, necrotic core, and calcification, respectively). In particular, NC is multiplied by 0.75 and CA is multiplied by 0.5 before summing these values. The fibrous cap status is then accounted for by multiplying the intermediate value A by FCS to produce a second intermediate value B. Finally, the ARS is determined by accounting for the fibrous cap composition. In particular, the intermediate value B is multiplied by the value: $(1+0.5\times[FCC-1])$. Obviously, the particulars of this calculation are broken up to better elucidate the present invention and to highlight the impact that the various components contribute to the final ARS. The details of the particular weightings and the specific combination of the values should also be clear to the artisan that alternative scoring systems may be used without departing from the teaching of the present invention.

As an example, refer to FIG. 2, which shows a ruptured fibrous cap, a juxtaluminal hemorrhage, deep necrotic core, and calcification. Assume the fibrous cap is determined to be collagen so that FCC=1; FCS=2; HE=2; NC=1 and CA=1. Then A is 3.25, B is 6.50 and the ARS is 6.5.

To validate this scoring system, the histology and MRI data were obtained from 34 patients who were scheduled for a carotid endarterectomy. A 1.5T MR scanner was used to obtain pre-contrast images (TOF, T1, PD, and T2 weighted) and post-contrast T1WI MRI (6-10 minutes after contrast administration). Two hundred and sixty locations matched between MRI and excised histology specimens were selected. Cohen's Kappa and Pearson correlation was used to determine agreement and association between MRI and histology results. The matched MR images and histology slices showed moderate to good agreement for FC status, FC composition, hemorrhage, necrotic core, and calcification, with the following respective Cohen's Kappa values—0.84, 0.82, 0.73, 0.76, and 0.77, respectively. The Pearson Correlation values for Scores A, B, and ARS were 0.84, 0.86, and 0.87, respectively. Interclass correlation coefficient values for Scores A, B, and C were 0.84, 0.87, and 0.87, respectively. These strong correlations indicate that MRI-based atherosclerosis scoring is able to provide similar information as histology.

The resulting ARS provides a quick, straightforward, and clinically useful characterization of the risk associated with an atherosclerotic deposit in a patient's artery, wherein higher ARS indicate a greater risk that the atherosclerosis will precipitate a clinical event (e.g., stroke or heart attack) in the near term.

While the preferred embodiment of the invention has been illustrated and described, it will be appreciated that various changes can be made therein without departing from the spirit and scope of the invention. It is contemplated, for example, that alternative methods of defining the juxtaluminal region may be utilized to improve the risk scoring and/or to better match data for arteries other than the carotid artery. For example, a set depth, such as one millimeter, may be alternatively utilized. It is also contemplated that the details of weighting and combining the scores for FCC, FCS, NC, HE, and CA may be modified without departing from the present invention—for example, to more closely correlate the calculated ARS with clinical outcomes. Obviously the particular values used in the ARS may be modified, for example, to normalize the ARS to a desired range.

In another simplified embodiment of the invention, for example, the above-described scores were assigned for NC, HE and CA (see, FIG. 4), but the fibrous cap was scored only for its status, with FCS assigned a value of zero indicating no fibrous cap, a value of one indicating an intact fibrous cap, and a value of two indicating a ruptured fibrous cap. The ARS was then simply calculated by weighting FCS and HE by two, and summing the values, i.e. ARS=2×FCS+2×HE+NC+CA. Again referring to FIG. 2 wherein FCS=2; HE=2; NC=1 and CA=1. In this simplified alternative embodiment the calculated ARS is 10.

It is also contemplated that the ARS would be used in conjunction with other clinical information including patient history, habits, and the like. For example, a modified ARS may be calculated that further incorporates such information.

The invention claimed is:

1. A method for characterizing the risk associated with atherosclerosis comprising:
   imaging a cross-section of an artery containing atherosclerotic plaque with a fibrous cap to generate at least one image;
   identifying in the at least one image components of the plaque;
   determining from the at least one image which of the identified components are located in a juxtaluminal region of the artery;
   determining from the at least one image a fibrous cap status;
   determining from the at least one image a fibrous cap composition; and
   calculating an atherosclerotic risk score that is dependent on the fibrous cap status, the fibrous cap composition, and the presence of components in the juxtaluminal region of the artery.

2. The method of claim 1, wherein the identified components comprise one or more of a necrotic core, a hemorrhage, and a calcification.

3. The method of claim 2, wherein the imaging is accomplished using at least one of magnetic resonance imaging, computed tomography, and ultrasound.

4. The method of claim 3, wherein the juxtaluminal region is the region approximately one-third of the thickness of the imaged portion of the atherosclerotic plaque.

5. The method of claim 1, wherein the composition of the fibrous cap region is either collagen or mixed tissue.

6. The method of claim 1, wherein the status of the fibrous cap is either ruptured or intact.

7. The method of claim 1, wherein the atherosclerotic risk score is further based on the presence of one or more of the necrotic core, the hemorrhage, and the calcification in regions of the artery located away from the juxtaluminal region.

8. The method of claim 1, wherein a score is assigned for each of the following attributes:
   (i) the fibrous cap status;
   (ii) the fibrous cap composition;
   (iii) the presence of necrotic core;
   (iv) the presence of hemorrhage; and
   (v) the presence of calcification; and further,
   wherein these scores are combined to determine the atherosclerotic risk score.

9. The method of claim 8, wherein each of the attributes is assigned a score between zero and two.

10. The method of claim 9, wherein the assigned values are combined by weighting and then summing the scores assigned to the presence of necrotic core, hemorrhage, and calcification and multiplying the sum by factors containing the scores assigned for the fibrous cap status and the fibrous cap composition.

11. A method for calculating an atherosclerosis risk score comprising:
   imaging a cross section of an artery to generate an image;
   identifying in the artery a lumen and an outer wall, wherein the region between the lumen and the outer wall comprises an atherosclerotic plaque deposit;
   defining a region of the atherosclerotic plaque deposit nearest the lumen as a juxtaluminal region;
   identifying compositional components in the atherosclerotic plaque deposit;
   identifying the status and composition of a fibrous cap portion of the atherosclerotic plaque deposit;
   assigning a first set of scores based on the presence and location of the identified compositional components;
   assigning a second set of scores based on the status and composition of the fibrous cap; and
   mathematically combining the first and second set of scores to produce an atherosclerotic risk score.

12. The method of claim 11, wherein the identified compositional components include one or more of a necrotic core, a hemorrhage, and a calcification.

13. The method of claim 12, wherein the imaging is accomplished using at least one of magnetic resonance imaging, computed tomography, and ultrasound.

14. The method of claim 13, wherein the juxtaluminal region is defined to be a region from the lumen surface and extending to approximately one-third of the thickness of the atherosclerotic plaque.

15. The method of claim 11, wherein the composition of the fibrous cap region is either collagen or mixed tissue.

16. The method of claim 11, wherein the status of the fibrous cap is either ruptured or intact.

17. The method of claim 11, wherein each of the first set of scores is integer values between zero and two.

18. The method of claim 11, wherein the first set of scores is additively combined to produce a first intermediate value and the second set of scores is multiplicatively combined with the first intermediate value.

* * * * *

UNITED STATES PATENT AND TRADEMARK OFFICE
CERTIFICATE OF CORRECTION

PATENT NO. : 7,340,083 B2
APPLICATION NO. : 11/172415
DATED : March 4, 2008
INVENTOR(S) : C. Yuan et al.

It is certified that error appears in the above-identified patent and that said Letters Patent is hereby corrected as shown below:

| COLUMN | LINE | ERROR |
|---|---|---|
| (56) Pg. 1, col. 2 | Refs. Cited (Other Publs., Item 2) | "Cariod" should read --Carotid-- |
| (56) Pg. 2, col. 1 | Refs. Cited (Other Publs., Item 5) | "Imgaing" should read --Imaging-- |
| (56) Pg. 2, col. 1 | Refs. Cited (Other Publs., Item 7) | "Artheriosclerosis," should read --Arteriosclerosis,-- |

Signed and Sealed this

Eighteenth Day of November, 2008

JON W. DUDAS
*Director of the United States Patent and Trademark Office*